(12) United States Patent
Young et al.

(10) Patent No.: US 10,905,789 B2
(45) Date of Patent: Feb. 2, 2021

(54) FAN DIFFUSER

(71) Applicant: Aeron Lifestyle Technology, Inc., Fairfield, IA (US)

(72) Inventors: Christopher Young, Rushville, IL (US); Jerome L. Clock, Hampton, IA (US); Monica Herr Hadley, Fairfield, IA (US)

(73) Assignee: AERON LIFESTYLE TECHNOLOGY, INC., Fairfield, IA (US)

( * ) Notice: Subject to any disclaimer, the term of this patent is extended or adjusted under 35 U.S.C. 154(b) by 238 days.

(21) Appl. No.: 16/228,369

(22) Filed: Dec. 20, 2018

(65) Prior Publication Data
US 2020/0197558 A1    Jun. 25, 2020

(51) Int. Cl.
| | |
|---|---|
| *A61L 9/12* | (2006.01) |
| *B01F 3/04* | (2006.01) |
| *A61L 9/14* | (2006.01) |
| *B05B 11/00* | (2006.01) |
| *F04D 25/06* | (2006.01) |

(52) U.S. Cl.
CPC .................. *A61L 9/14* (2013.01); *A61L 9/122* (2013.01); *B01F 3/04085* (2013.01); *B05B 11/30* (2013.01); *A61L 2209/134* (2013.01); *F04D 25/0673* (2013.01)

(58) Field of Classification Search
CPC .... A61L 9/12; A61L 9/122; B01F 3/04; B01F 3/04085
See application file for complete search history.

(56) References Cited

U.S. PATENT DOCUMENTS

2007/0158456 A1    7/2007  Spector

FOREIGN PATENT DOCUMENTS

| FR | 2961698 A1 | 12/2011 | |
|---|---|---|---|
| GB | 2423253 A | * 8/2006 | ............. A61L 9/122 |
| WO | 2011128604 A1 | 10/2011 | |

OTHER PUBLICATIONS

FR2961698 (A1)—English Transalation.

* cited by examiner

*Primary Examiner* — Robert A Hopkins
(74) *Attorney, Agent, or Firm* — Zarley Law Firm, P.L.C.

(57) ABSTRACT

An oil fan diffuser having a housing with a first section and a second section. A power source such as a plurality of batteries are disposed within the second section. Disposed within the first section is a fan, an inner housing, a fragrance emitting member, a retaining member, and an inverted fragrance bottle.

6 Claims, 3 Drawing Sheets

FAN DIFFUSER

BACKGROUND OF THE INVENTION

The present invention is directed to an essential oil fan diffuser, and more particularly, a self-regulating oil fan diffuser that uses a gravity fed fluid dispersion.

Essential oil diffusers are known in the art and generally disperses oils into the air to be inhaled and absorbed by the body. As an added benefit, most essential oils also emit a pleasant scent into the air when distributed via a diffuser, also purifying the air.

Some essential oil diffusers distribute the oils via evaporation and use a fan to generate air flow causing the oil to evaporate into the air. Typically, the oil is held in an absorbent material such as a pad or a wick, so that the air flow causes the oil to evaporate in a controlled environment. While useful, these types of diffusers require frequent and repeated manual reapplication of the oil to the absorbent material.

Accordingly, a diffuser is needed in the art that addresses this deficiency.

An objective of the present invention is to provide an essential oil fan diffuser that is self-regulating.

Another objective of the present invention is to provide an essential oil fan diffuser having a gravity fed fluid disbursement.

A still further objective of the present invention is to provide an essential oil fan diffuser that does not require frequent manual refills.

These and other objectives will be apparent to those having ordinary skill in the art based upon the following written description, drawings, and claims.

SUMMARY OF THE INVENTION

An essential oil fan diffuser has a housing having an upper and a lower section. Disposed within the lower section is a power source such as replaceable batteries. Operatively connected to a top wall of the lower section is a fan. An inner housing covers the fan and is connected to the lower section.

Connected to the inner housing is a retaining member. The retaining member holds a fragrance emitting member between the top wall of the inner housing and the retaining member. The retaining member also holds a fragrance bottle in an inverted position. The fragrance emitting member is positioned to cover and seal the opening to the inverted fragrance bottle.

The top section is removably connected to the bottom section and covers the fan, inner housing, fragrance emitting member, and retaining member. The top section has a plurality of vents in a top wall. When assembled, the fan blows air through vents in the top wall of the inner housing causing oil, absorbed by the fragrance emitting member from the bottle to evaporate into the air through the vents in the top section.

DETAILED DESCRIPTION OF THE PREFERRED EMBODIMENTS

Figures 1, 2:
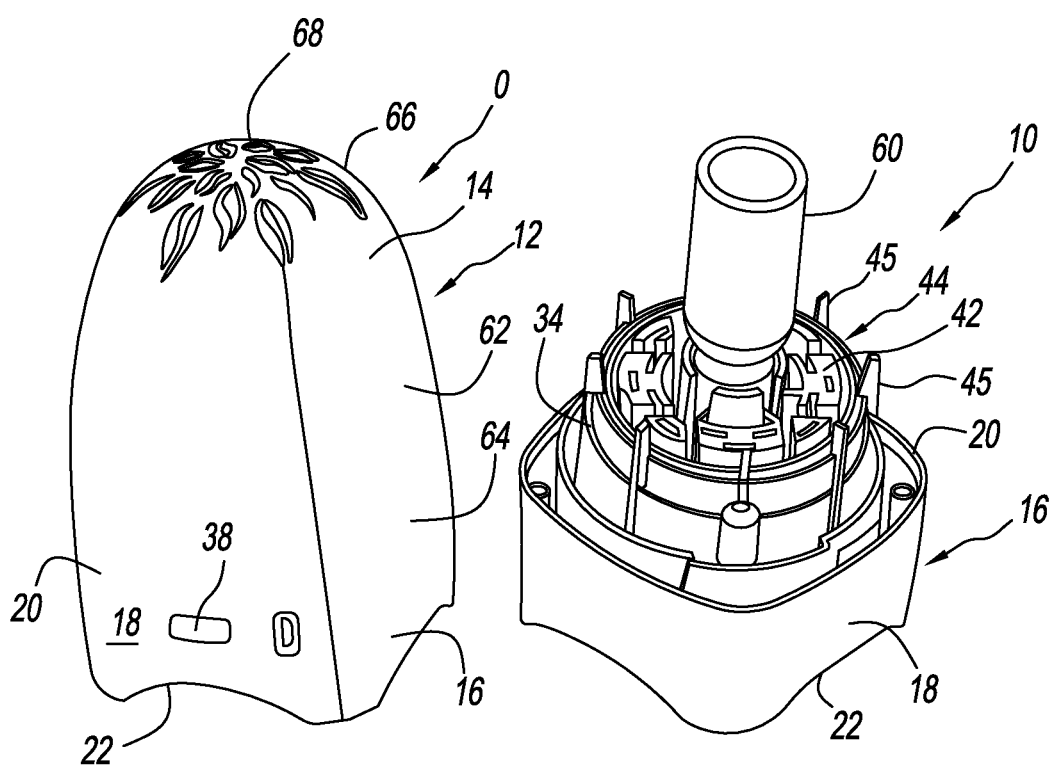
FIG. 1 is a perspective view of an essential oil fan diffuser.
FIG. 2 is a perspective view of an uncovered essential oil fan diffuser.
Figure 3:
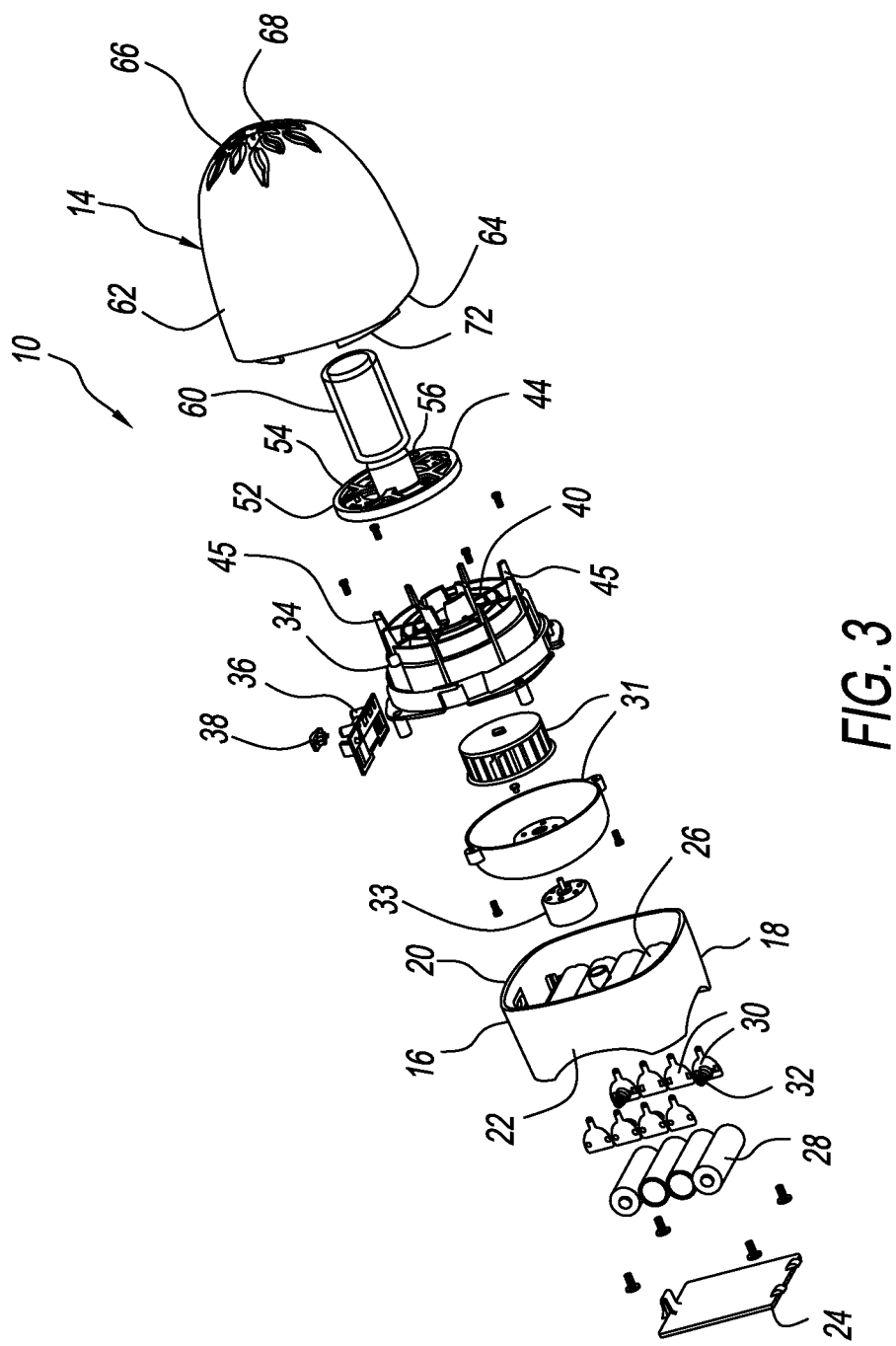
FIG. 3 is an exploded perspective view of an essential oil fan diffuser.
Figure 4:
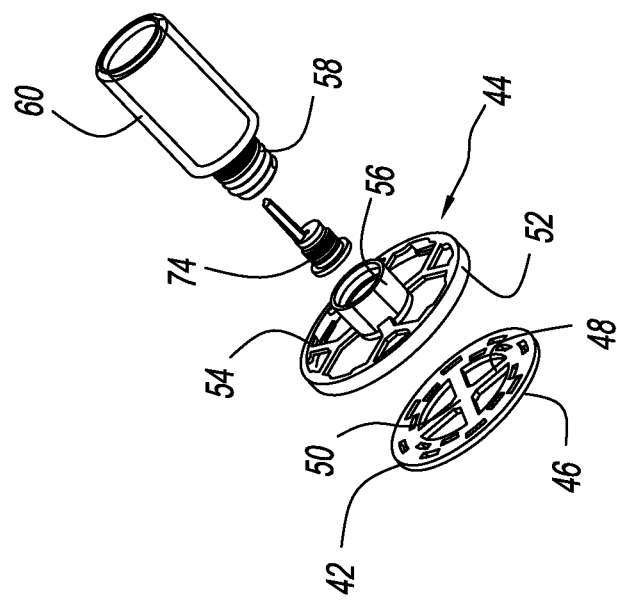
FIG. 4 is an exploded perspective view of a retainer member and fragrance emitting member.
Figure 4:
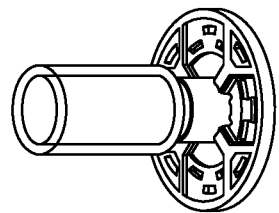
Figure 4:
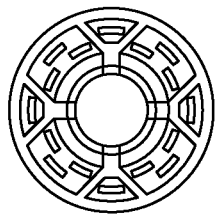
Figure 4:
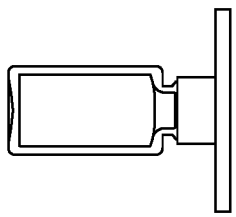

Referring to the Figures, an oil fan diffuser 10 has a housing 12 that includes a first or upper section 14 and a second or lower section 16. The housing is of any size, shape, and structure. In one example, the lower section 16 has a side wall 18 with a top edge 20 and a bottom edge 22, and a bottom wall (not shown). The bottom wall has an opening (not shown) covered by a removable door 24. The lower section 16 also has a horizontal wall 26 midway on the side wall 18 that along with the bottom wall and the side wall 18, forms a chamber. Disposed in the chamber are a plurality of batteries 28, contacts 30, and contact springs 32. The horizontal wall 26 can be formed to partially receive the batteries 28.

Operatively mounted to the horizontal wall 26 is a fan 31 driven by a motor 33. An inner housing 34 covers the fan 31 and is connected to the lower section 16 of the housing 12. A circuit board 36 having an activation button 38 is connected to the fan 31 and is disposed within the lower section and the button 38 extends through a side wall 18. The circuit board is connected to the batteries 28 and the motor 32.

The inner housing 34 has a top wall 40 having a plurality of vents to permit air flow. The top wall 40 is also formed and adapted to receive a fragrance emitting member 42 such as a pad or the like and a retaining member 44. In particular, the inner housing 34 has a plurality of prongs 45 spaced around the outer perimeter of the top wall 40 that extend upwardly to frictionally receive the retaining member 44. The pad 42 is of any size, shape, and structure and in the example shown is circular with an outer ring 46 with a plurality of radial members 48 that extend from a center section 50 to the outer ring 46. The outer ring 46 has a plurality of vents.

The retaining member 44 is likewise of any size, shape, and structure. In the example shown the retaining member 44 is wheel shaped having an outer rim 52 and a plurality of spokes 54 radially extending from a central hub or connector 56 to the outer rim 52. Preferably, the spokes 54 are y-shaped. The connector 56 is cylindrical and extends away from the lower section 16 of the housing 12. The connector 56 is formed to receive, either threadably or by friction fit, a neck 58 of a fragrance bottle 60 that retains a fragrance liquid.

The outer rim 52 has a depth or wall that extends toward the lower section 16 and that receives the fragrance emitting member 42. The upper section 14 has a side wall 62 with a lower edge 64 and a top wall 66 having a plurality of vents 68. The lower edge 64 has a plurality of projections 72 that extend downwardly toward the lower section 16 and are received within the side walls 18 of the lower section 16. The upper section 14 covers the retaining member 44, the fragrance emitting member 42, and the inner housing 34.

In operation, the fragrance emitting member 42 is placed within the outer rim 52 of the retaining member 44. The neck 58 of the bottle 60 is then attached to the connector 56 of the retaining member 44. When attached, the fragrance emitting member 42 is held against the bottle 60 orifice to provide a seal to prevent the liquid from flowing freely out of the bottle 60 when the bottle 60 is turned upside down.

Once the bottle 60 is attached to the retaining member 44, the retaining member 44 is connected to the inner housing such that the fragrance emitting member 42 is positioned between the top wall 40 of the inner housing 34 and completely below the bottle 60, which is in an upside down or inverted position. Due to gravity and with the aid of a standard bottle dropper 74, the fragrance liquid flows out of the bottle 60 and onto the fragrance emitting member 42 positioned below the bottle 60.

The fragrance emitting member 42 preferably is made of an absorbent material and due to its shape the liquid is absorbed by the center section 50, then by the radial members 48, and finally by the outer ring 46. The fan 30 is activated using activation button 38 which causes air to flow through the vents in the top wall 40 of the inner housing 34, past the fragrance emitting member 42 where fragrant vapors of the evaporating liquid are collected, and finally through the vents 68 in the top wall 66 of the upper section 14. In this manner the oil fan diffuser provides a self-regulating gravity fed fluid dispersion where one can set and then forget about the diffuser until the dispersion uses all the liquid in the bottle. There is no need to manually refill the diffuser once the diffuser is set up.

Accordingly, an oil fan diffuser has been disclosed that at the very least meets all of the stated objectives.

What is claimed is:

1. A fan diffuser, comprising:
    a housing having a first section removably connected to a second section;
    a fan disposed within the first section and operatively connected to a second section; and
    a retaining member disposed within the first section and adapted to hold a fragrance bottle in an inverted position and a fragrance emitting member below the bottle and above the fan.

2. The diffuser of claim 1 wherein the first section of the housing has a top wall having a plurality of vents.

3. The diffuser of claim 1 wherein the retaining member has an outer rim, a central connector, and a plurality of spokes that extend between the central connector and the outer rim.

4. The diffuser of claim 1 wherein the fragrance emitting member is positioned to seal the fragrance bottle.

5. The diffuser of claim 1 wherein the fragrance emitting member has an outer ring, a central section, and a plurality of radial members that extend between the outer ring and the central section.

6. The diffuser of claim 1 wherein an inner housing covers the fan.

* * * * *